US012611669B2

(12) United States Patent
De Angelis et al.

(10) Patent No.: US 12,611,669 B2
(45) Date of Patent: Apr. 28, 2026

(54) MICROFLUIDIC DEVICE AND METHODS FOR USING SUCH DEVICE

(71) Applicant: Fondazione Istituto Italiano di Tecnologia, Genoa (IT)

(72) Inventors: Francesco De Angelis, Genoa (IT); Michele Dipalo, Genoa (IT); Francesco Tantussi, Genoa (IT); Andrea Barbaglia, Genoa (IT); Andrea Toma, Genoa (IT)

(73) Assignee: Fondazione Istituto Italiano di Tecnologia, Genoa (IT)

( * ) Notice: Subject to any disclaimer, the term of this patent is extended or adjusted under 35 U.S.C. 154(b) by 950 days.

(21) Appl. No.: 17/793,713

(22) PCT Filed: Jan. 21, 2021

(86) PCT No.: PCT/IB2021/050458
§ 371 (c)(1),
(2) Date: Jul. 19, 2022

(87) PCT Pub. No.: WO2021/148979
PCT Pub. Date: Jul. 29, 2021

(65) Prior Publication Data
US 2023/0051647 A1     Feb. 16, 2023

(30) Foreign Application Priority Data
Jan. 22, 2020    (IT) ........................ 102020000001219

(51) Int. Cl.
*B01L 3/00*        (2006.01)
*G01N 33/487*    (2006.01)
(52) U.S. Cl.
CPC ..... B01L 3/50273 (2013.01); B01L 3/502715 (2013.01); B01L 3/502761 (2013.01);
(Continued)

(58) Field of Classification Search
CPC ........... B01L 3/50273; B01L 3/502715; B01L 3/502761; B01L 2300/0645;
(Continued)

(56) References Cited

U.S. PATENT DOCUMENTS

2022/0032296 A1*    2/2022   De Angelis ....... B01L 3/502707
2023/0060283 A1*    3/2023   De Angelis ........ G01N 33/5005

FOREIGN PATENT DOCUMENTS

WO      WO 2020/058833         3/2020

OTHER PUBLICATIONS

Search Report and Written Opinion dated Jun. 14, 2021; Application No. PCT/IB2021/050458; 18 pages.
(Continued)

*Primary Examiner* — Jennifer Wecker
*Assistant Examiner* — Britney N. Washington
(74) *Attorney, Agent, or Firm* — RANKIN, HILL & CLARK LLP; Erik J. Overberger

(57)                    ABSTRACT

A microfluidic device comprises a lower layer that is electrically conductive and transparent with respect to an incident optical beam, an upper layer, comprising first portions that are electrically conductive and second portions that are electrically insulating, adjacent and alternated to the first ones; a compartment seamlessly extending between the lower layer and the upper layer; the compartment contains a filler medium configured to emit an optical emission beam and markers dispersed in the filler medium, which are electrically charged and are adapted to move inside the compartment in all directions according to the intensity of the electrical signal applied to the first portions, the filler medium is configured to interact with the markers to increase or decrease the intensity of the optical emission beam according to the local concentration of the markers.

14 Claims, 2 Drawing Sheets

(52) U.S. Cl.
CPC ................... *G01N 33/48728* (2013.01); *B01L 2300/0645* (2013.01); *B01L 2400/0415* (2013.01)

(58) Field of Classification Search
CPC ..... B01L 2400/0415; B01L 2300/0887; G01N 33/48728; G01N 33/526
See application file for complete search history.

(56)                    References Cited

OTHER PUBLICATIONS

Jiayi Zhang et al: Optical Detection of Brain Cell Activity Using Plasmonic Gold Nanoparticles , Nano Letters, vol. 9, No. 2, Feb. 11, 2009 (Feb. 11, 2009), pp. 519-524; 6 pages.

Andrea Cerea et al: Selective intracellular delivery and intracellular recordings combined in MEA biosensors, Lab on a Chip, vol. 18, No. 22, Jan. 1, 2018 (Jan. 1, 2018), pp. 3492-3500; 9 pages.

Andrea Cerea et al: Selective intracellular delivery and intracellular recordings combined on MEA biosensors , arxiv.org, Cornell University Library, 201 Olin Library Cornell University Ithaca, NY 14853, Aug. 23, 2018 (Aug. 23, 2018), XP081176106, p. 4-p. 12; 20 pages.

Ballini Marco et al: A 1024-Channel CMOS Microelectrode Array With 26,400 Electrodes for Recording and Stimulation of Electrogenic Cells In Vitro , IEEE Journal of Solid-State Circuits, IEEE, USA, vol. 49, No. 11, Nov. 1, 2014 (Nov. 1, 2014), pp. 2705-2719; 15 pages.

Michele Dipalo et al: Intracellular and Extracellular Recording of Spontaneous Action Potentials in Mammalian Neurons and Cardiac Cells with 3D Plasmonic Nanoelectrodes , Nano Letters, vol. 17, No. 6, May 24, 2017 (May 24, 2017), pp. 3932-3939; 8 pages.

Parameswaran Ramya et al: Scalable breakthrough, Nature Nanotechnology, Nature Pub. Group, Inc, London, vol. 13, No. 10, Aug. 13, 2018 (Aug. 13, 2018); 2 pages.

Michele Dipalo et al: Plasmonic meta-electrodes allow intracellular recordings at network level on high-density CMOS-multi-electrode arrays, Nature Nanotechnology, Aug. 13, 2018 (Aug. 13, 2018); 12 pages.

* cited by examiner

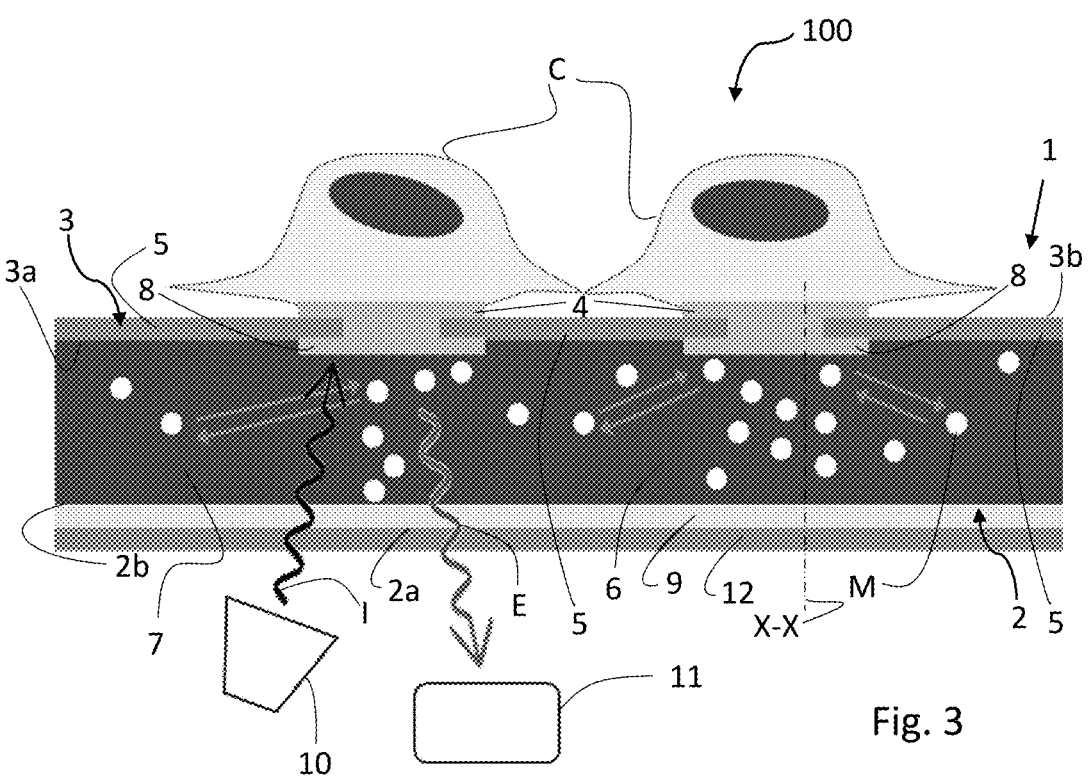
Fig. 3
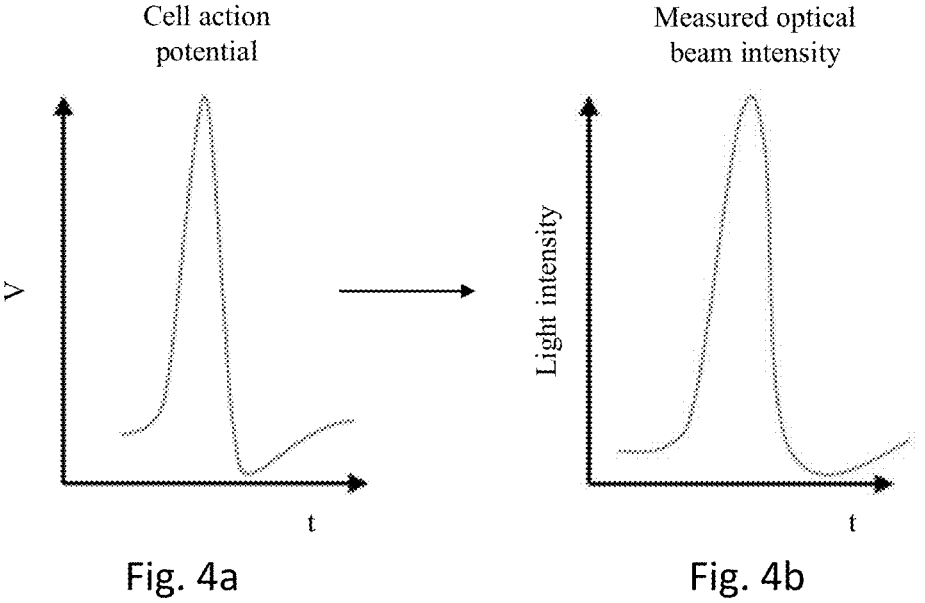
Cell action potential
Measured optical beam intensity
Fig. 4a                    Fig. 4b

MICROFLUIDIC DEVICE AND METHODS FOR USING SUCH DEVICE

TECHNICAL FIELD

The present invention relates to a microfluidic device and methods for using such a device.

The microfluidic device of the present invention finds particular application in measuring the action potential of an in vitro cell.

The microfluidic device of the present invention also finds particular application in data storage.

BACKGROUND

The action potential is a signal of the electro-genic cells, that is, those cells capable of modifying the permeability of their membrane to certain ions in response to electrical or mechanical stimuli. The action potential is generated when the trans-membrane ion potential exceeds a certain threshold, and is then transmitted to send information, to regulate muscle or hormonal response.

Consequently, in order to understand the behaviour of some cells or to evaluate cell activity in a tissue, it is useful to know the course of the action potential of these cells.

The action potential can be obtained by direct measurements, by detecting the electrical signal deriving from cellular excitation with electrodes inserted inside the cell. Alternatively, the action potential can be obtained indirectly, by acquiring another type of signal and subsequently converting the latter into action potential. Known indirect methods exploit fully optical approaches, i.e. based on the reconstruction of the course of the action potential starting from a detected optical signal. Indirect optical methods are preferred compared to direct electrical methods in that they allow a higher spatial resolution to be obtained, however they are invasive in that they require the insertion of molecules inside the cells.

With regard to data storage, the most widespread memory devices are nowadays are based on CMOS technology. These devices, however, have physical limitations in terms of scalability and, consequently, of memory unit density per chip. New data storage devices are therefore sought to address the large and growing amount of data produced by modern society.

The previous patent application IT102018000008717, filed by the same Applicant and not yet available to the public at the moment of the filing of the present patent application, describes a microfluidic device for measuring the action potential which exploits an indirect optical method. This device comprises a conductive upper layer, arranged to receive one or more electrical signals, and a transparent lower layer, also conductive. The device also comprises shielding portions that are opaque with respect to the incident optical beam and arranged between the upper layer and the lower layer. The shielding portions have one or more through openings. The device comprises one or more compartments containing a filler medium and markers, such as fluorophores, dispersed in the filler medium. Each compartment comprises one or more lower chambers and an upper chamber in fluid communication between them through the one or more through openings of the shielding portions. Each lower chamber extends between a respective through opening and the lower layer, and each upper chamber extends between a respective through opening and the upper layer. The cells to be analysed are arranged on the upper layer where they supply the electrical signal through their action potential. The markers are electrically charged and are intended to move between the upper chamber and one or more lower chambers in variable amounts according to the intensity of the electrical signal applied to the upper layer by one or more cells. The markers emit an optical emission beam when they are lit in the lower chamber by an incident optical beam. Since the concentration of the markers in the lower chamber varies according to the electrical signal present on the upper layer, the intensity of the emission signal provides an indication of the action potential of the cells.

The microfluidic device structured as mentioned above allows to detect the electrical activity of the cells in their physiological conditions, since it does not require any invasive modification of the cells or the use of a circuit. Moreover, the method using such a device offers a good sensitivity in measuring the action potential and the spatial resolution obtained is high.

Problem of the Prior Art

Although the measurement using such a device is based on a very efficient principle and has the advantages mentioned above, the realisation of such a microfluidic device is however long and expensive due to the complexity of the structure.

SUMMARY OF THE INVENTION

The main object of the present invention is to provide a microfluidic device for measuring the cellular electrical activity which maintains the advantages of the microfluidic device described above but which has a simplified structure and is easier to produce.

A further object of the present invention is to provide a microfluidic device which allows to improve the spatial resolution during the step of detection of the cellular action potential with respect to the microfluidic device mentioned above.

A further object of the present invention is to provide a microfluidic device for storing data which allows a higher density of memory elements and a higher writing and reading speed of the data item than known devices.

The technical task specified and the objects specified are substantially achieved by a microfluidic device comprising the technical features set forth in one or more of the appended claims.

Thanks to the present invention it is possible to produce a microfluidic device that is easier and more economical to realise, while maintaining the efficiency and precision in the measurement of the microfluidic device mentioned above.

Thanks to the present invention, it is possible to produce a microfluidic device having a better spatial resolution than the above-mentioned microfluidic device.

Thanks to the device of the present invention it is possible to obtain a complete real-time vision of the movement of the markers inside the compartment according to the action potential. As a result, it is possible to have precise information on the mode and propagation rate of the electrical signal of the cells.

Thanks to the present invention it is also possible to realise a microfluidic device, an apparatus comprising such a device and a method which allow to effectively detect the action potential of the cells.

Thanks to the present invention it is also possible to realise a microfluidic device and a method for storing data which allow a high density of memory elements and a fast writing/reading of the data item.

BRIEF DESCRIPTION OF THE DRAWINGS

The characteristics and advantages of the present invention will become clear from the following detailed description of a possible practical embodiment, illustrated by way of non-limiting example in the set of drawings, wherein:

FIG. 3 shows a schematic view of an application of an apparatus comprising a microfluidic device in accordance with the present invention;

FIGS. 4a and 4b show, respectively, the curves of an electrical signal applied to the microfluidic device of FIG. 3 and of an optical emission signal emitted by the device itself.

DETAILED DESCRIPTION

Figures 1A, 1B, 2:
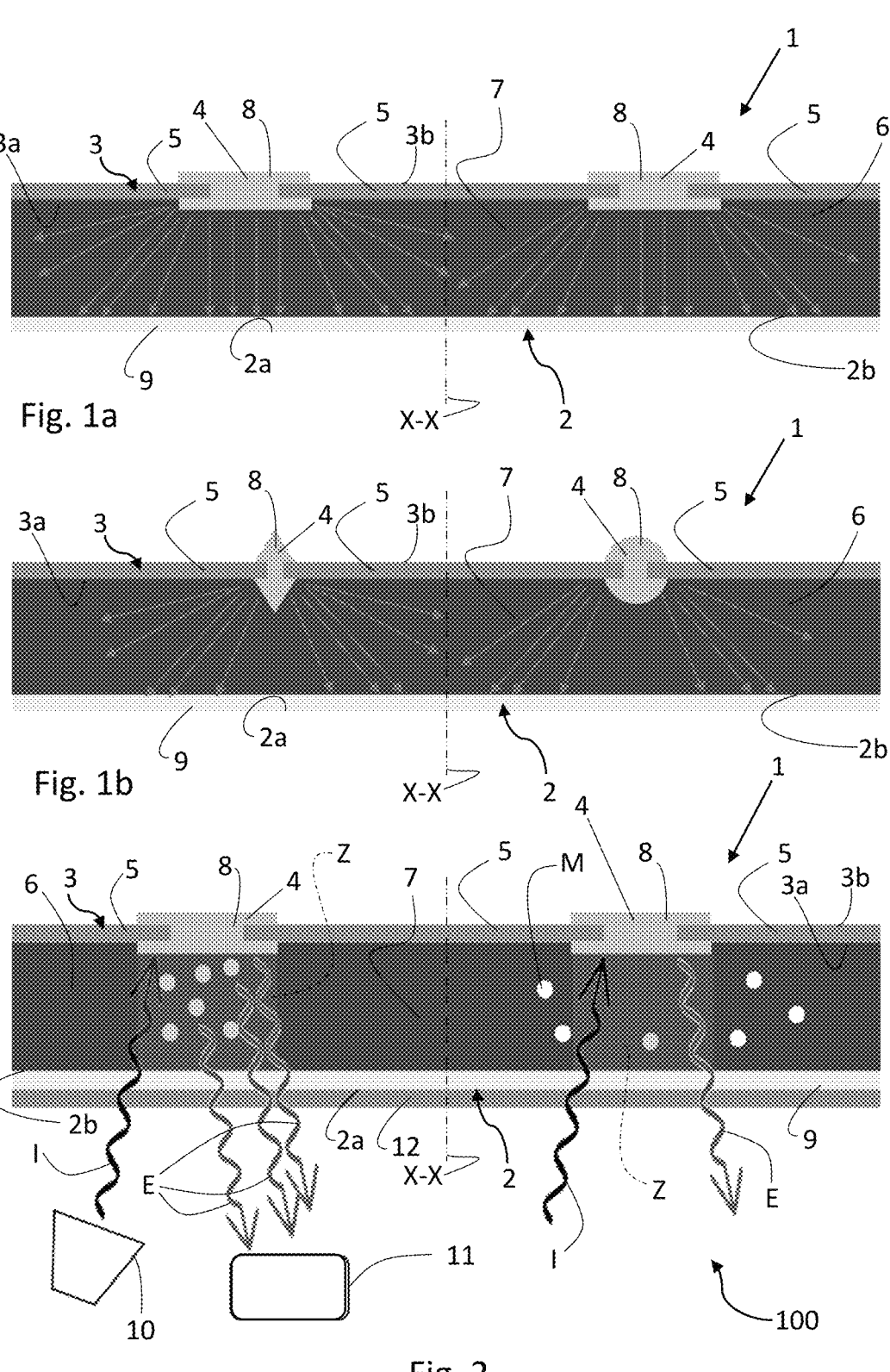
FIGS. 1a and 1b show a schematic view of the structure of a microfluidic device in accordance with the present invention.
FIG. 2 shows a schematic view of an apparatus comprising a microfluidic device in accordance with the present invention.

The accompanying FIGS. 1 to 3 show a microfluidic device 1 according to the present invention.

Two different embodiments of the microfluidic device 1 are described in the continuation of the present description.

According to a first embodiment, the microfluidic device 1 comprises a lower layer 2 and an upper layer 3. The lower layer 2 has a lower surface 2a and an upper surface 2b opposite the lower surface 2a. The upper layer 3 has a lower surface 3a and an upper surface 3b opposite the lower surface 3a.

The lower layer 2 is electrically conductive and is partially or totally transparent with respect to an incident optical beam I generated by an optical source 10.

The upper layer 3 comprises first portions 4 and second portions 5, adjacent and alternated between them.

The first portions 4 are electrically conductive and are configured to receive an electrical signal. The second portions 5 are electrically insulating. Preferably, the first portions 4 have micrometric or nanometric dimensions and are spaced between them at a distance between 1 and 100 μm. In other words, the second portions 5 have a length between 1 and 100 μm.

The lower layer 2 and the upper layer 3 are spaced between them along a direction X-X transverse to the planes on which the lower layer 2 and the upper layer 3 extend.

The microfluidic device 1 also comprises a compartment 6 interposed between the lower layer 2 and the upper layer 3. In particular, the compartment 6 faces the surface 2b and the surface 3a of the lower 2 and upper 3 layers.

Preferably, the compartment 6 seamlessly extends between the lower layer 2 and the upper layer 3 throughout the extension of the lower layer 2 and the upper layer 3.

The compartment 6 comprises a filler medium 7 that is transparent with respect to the incident optical beam I. In accordance with a preferred embodiment, the filler medium 7 is a substance in liquid form. In accordance with another alternative embodiment, the filler medium 7 is a substance in gel or a solid form.

The compartment 6 also comprises markers M, homogeneously dispersed in the filler medium 7. In particular, in accordance with this first embodiment, the markers M are adapted to emit an optical emission beam E at an emission wavelength when they are lit by the incident optical beam I.

According to a preferred embodiment, the markers M are fluorophores of predefined spectral output.

In accordance with a preferred embodiment, the markers M are in the form of nanoparticles of predetermined molecular weight and dimensions. The markers M can have different shapes. For example, the markers M may be quantum dots or nanorod.

It should be noted that the markers M have a predefined electrical charge and are adapted to move in the presence of an electrical signal. In particular, when an electrical signal is applied to the first portions 4, the markers M move inside the compartment 6 in variable amounts in all directions according to the intensity of the electrical signal applied. Depending on the sign and on the electric charge module, the movement of the markers M inside the compartment 6 varies, and consequently the local concentration of markers M inside the compartment 6 varies.

According to a preferred embodiment of the invention, the upper layer 3 comprises an upper electrode 8. Preferably, the first portions 4 comprise a plurality of upper electrodes 8. More preferably, the first portions 4 consist of a plurality of upper electrodes 8. Each upper electrode 8 is configured to receive a respective electrical signal.

Preferably, the upper electrodes 8 may have different shapes, as shown in FIGS. 1a and 1b. For example, the upper electrodes 8 have a conformation selected from plate, polygonal, spheroidal or a combination thereof.

The lower layer 2 comprises a lower electrode 9. In particular, the lower layer 2 consists of a single lower electrode 9.

The upper electrodes 8 and the lower electrode 9 are electrically connected between them in an electric circuit or are floating.

According to a preferred embodiment shown in FIG. 3, the first portions 4 are configured to house at least a cell C. In particular, the cells C are arranged above the first portions 4. Preferably, the first portions 4 have such dimensions as to house one single cell C each. More preferably, the first portions 4 comprise a plurality of micro-electrodes or nano-electrodes each adapted to house a cell C or a portion of cell C. In accordance with this preferred embodiment, the first portions 4 are configured to receive the electrical signal of the action potential generated by the excited cell C.

Upon application of the electrical signal to the first portions 4, the markers M inside the compartment 6 are attracted or rejected by a first portion 4 on the basis of the sign of the potential applied thereto and on the basis of the electrical charge of the markers M. Accordingly, the markers M move along the field lines toward the first portions 4 by which they are attracted. In particular, the markers M move from and towards zones Z defined inside the compartment 6 and underlying the respective first portions 4 by which the markers M are rejected or attracted. Consequently, the concentration of the markers M in the various zones Z indicates the real-time electrical charge present in the first portions 4 by which the markers M are rejected or attracted.

The markers M present in the compartment 6 in the various zones Z, when they are hit by the incident optical beam I by an optical source 10, emit an optical emission beam E which crosses the lower layer 2 starting from the surface 2b and which can be received by an external detection optical device 11.

It should be noted that the optical source 10 is preferably external to the microfluidic device 1. According to an alternative embodiment, the optical source 10 is internal to the microfluidic device 1, i.e. integrated therewith, and comprises, for example, micro-LED or other similar technologies known per se.

The intensity of the optical emission beam E depends on the concentration of the markers M in a given zone Z. Therefore, from the light signal detected by the detection optical device 11 it is possible to observe the behaviour of the electrical signal applied on the first portions 4. In the case where the electrical signal is generated by a single cell C, it is possible to observe the trend of the action potential of said cell C.

The microfluidic device 1, with respect to the devices known in the state of the art or to the one described in the above-mentioned patent application, allows to obtain a good spatial resolution, thanks to the homogeneous structure that it has, and in particular to the compartment 6 which seamlessly extends between the lower layer 2 and the upper layer 3.

According to a preferred embodiment, the first portions 4 are at least partially reflective with respect to the incident optical beam I. Preferably, at least the surfaces of the first portions 4 facing the compartment 6 are reflective with respect to the incident optical beam I. Advantageously, it is possible to intensify the emission effect of the markers M since they are also lit by the reflected incident optical beam I.

According to one embodiment, the second portions 5 are transparent with respect to the optical emission beam E. According to this embodiment, the optical emission beam E emitted by the markers M can also be detected through the upper layer 3 at the second portions 5. Advantageously, it is possible to observe the movements of the markers M also below the second portions 5 in order to obtain a complete vision over time of the movement of the markers M inside the compartment 6 according to the applied electrical signal. As a result, it is possible to have precise information on the mode and rate of propagation of the action potential of a cell C.

According to an embodiment that is alternative to the preceding one, the second portions 5 are at least partially reflective with respect to the incident optical beam I. This advantageously allows to intensify the emission effect of the markers, since they are also lit by the reflected incident optical beam I. According to this embodiment, the optical emission beam E is detected on the side of the lower layer 2, as occurs for the detection below the first portions 4. Advantageously, it is possible to observe the movements of the markers M also below the second portions 5 in order to obtain a complete vision over time of the movement of the markers M inside the compartment 6 according to the applied electrical signal. As a result, it is possible to have precise information on the mode and rate of propagation of the action potential of a cell C.

With particular reference to FIG. 4a, it should be noted a typical action potential signal, which is then converted into the optical signal shown in FIG. 4b.

As described above, the markers M have the possibility of moving inside the compartment 6 according to the electric potential applied to the first portions 4 and to the electrical charge, molecular weight and concentration of the markers M.

If the filler medium 7 is a liquid, in the presence of an electrical signal applied to the first portions 4 in the form of a pulse, the markers M move in the compartment 6 during the rising edge of the electrical signal and during the falling edge of the applied electrical signal. In this configuration, the optical emission beam E generated by the markers M in the zones Z allows to generate an optical signal representative of the pulse shape of the electrical signal applied to the first portions 4.

If the filler medium 7 is a gel or a solid, the markers M have the possibility of moving inside the compartment 6 in the presence of an applied electrical signal but they maintain their position in the compartment 6 in the absence of an electrical signal. The markers M maintain in any case the possibility of moving among the various zones Z in the presence of an electrical signal of sufficient intensity and opposite sign.

This solution is particularly advantageous for the realisation of optical read non-volatile memories with very low activation voltages of the order of a few mV. In the presence of gel or solid, in fact, the markers M remain in a fixed position in the zones Z of the compartment 6. The optical emission beam E generated by the markers M thus remains constant by virtue of their position and can be read several times, through the detection optical device 11.

It should be noted that the microfluidic device 1 of the present invention can also be used for realising a neuromorphic chip. In this configuration, each zone Z underlying an upper electrode 8 can represent a memory unit, for example a bit, whose value can be modified, i.e. written with a few mV applied to the first portions 4 and read, in optical mode, through the detection optical device 11. In greater detail, according to this configuration, the detected light signal, i.e. the optical emission beam E coming from each zone Z, can assume intensity values that are not discrete but continuous within a predetermined range. This range varies according to the concentration of the markers M in the zone Z, in particular it varies between 0, in which no markers M are present inside the zone Z, and a value given by the maximum concentration of markers M inside the zone Z.

In particular, the application of data storage by means of the microfluidic device 1 as described above is carried out by means of an electrical writing step of a data item and an optical reading step of the written data item.

In detail, the electrical writing of the data item is obtained by applying to the upper layer 3 an electrical signal, according to the intensity and in which direction the markers M move in variable amounts inside the filler medium 7. At the end of the application of the electrical signal, due to the gel or solid nature of the filler medium 7, the markers M remain stationary in the position in which they are located. Accordingly, the amounts of markers M that accumulate in the different zones Z of the compartment 6 indicate the applied potential and represent the stored data item.

It should be noted that, for this application, the electric potential pulses for writing the data item are generated by potential sources which are external to the microfluidic device 1, or alternatively by cells placed on the first portions 4, like for the application described above concerning the measurement of the cellular action potential.

The optical reading of the data item is carried out by illuminating the lower layer 2 with an incident optical beam I and by detecting the optical emission beam E emitted by the markers M accumulated in the different zones Z of the compartment 6. The intensity of the optical emission beam E coming from the various zones Z is proportional to the amount of markers M present, and therefore allows to read the stored data.

By way of example, if the electrical signal empties a zone Z from the markers M, the resulting optical emission beam E, relative to that zone Z, will be low and may be associated with the logic bit 0. If the electrical signal fills a respective zone Z with markers M, the resulting optical emission beam E, relative to that zone Z, will be high and can be associated with the logic bit 1. In the example in question, it should be noted how the sequential writing/reading of the zones Z, to which a respective logic number 0/1 is assigned, allows the data to be stored according to the binary code.

According to a particular embodiment, the microfluidic device 1 comprises markers M having spectral output and/or molecular weight and/or dimensions and/or shape and/or electrical charge and/or hydrodynamic radius different from each other.

In particular, the hydrodynamic radius is indicative of the friction due to the fluid to which the markers M are subjected, i.e., the speed at which the markers M move.

Markers M having different values of spectral output and/or molecular weight and/or dimensions and/or shape and/or electrical charge and/or hydrodynamic radius will consequently move differently inside the compartment 6. Therefore, it is possible to obtain continuous values and hence more precise measurements. In the case of measuring the action potential, for example, it is possible to measure both fast and low intensity potentials as well as longer and intense action potentials. Advantageously, it is possible to realise a memory with multi-state bits. It should be noted that in the case of application for memories, the potential may also not necessarily be generated by a biological element, such as the cell C.

It is also an object of the present invention an apparatus, indicated with 100 in FIGS. 2-3, comprising the microfluidic device 1 according to the first embodiment, an optical source 10 and a detection optical device 11.

The optical source 10 is configured to emit an incident optical beam I towards the lower layer 2, and in particular towards the lower surface 2*a*. Specifically, the optical source 10 is configured to direct the incident optical beam I towards the lower surface 2 at least at the first portions 4 of the microfluidic device 1, that is, at the zones Z that attract or reject the markers M.

The detection optical device 11, configured to detect the optical emission beam E, emitted by the markers M, is a CCD or CMOS device or a detector array. Preferably, the detection optical device 11 is filtered along the emission wavelength of the markers M so as to generate an optical signal representative of the electrical signal applied to the first portions 4, and optionally to the second portions 5, according to the intensity of the detected optical signal, that is, the optical emission beam E.

In accordance with a second embodiment, alternative to the one described so far, the microfluidic device 1 comprises a filler medium 7 configured to emit an optical emission beam E when lit by an incident optical beam I.

According to this embodiment, described below, the device 1 comprises a lower layer 2 and an upper layer 3. The lower layer 2 has a lower surface 2*a* and an upper surface 2*b* opposite the lower surface 2*a*. The upper layer 3 has a lower surface 3*a* and an upper surface 3*b* opposite the lower surface 3*a*.

The lower layer 2 is electrically conductive and is partially or totally transparent with respect to an incident optical beam I generated by an optical source 10.

The upper layer 3 comprises first portions 4 and second portions 5, adjacent and alternated between them.

The first portions 4 are electrically conductive and are configured to receive an electrical signal. The second portions 5 are electrically insulating. Preferably, the first portions 4 have micrometric or nanometric dimensions and are spaced between them at a distance between 1 and 100 μm. In other words, the second portions 5 have a length between 1 and 100 μm.

The lower layer 2 and the upper layer 3 are spaced between them along a direction X-X transverse to the planes on which the lower layer 2 and the upper layer 3 extend.

The microfluidic device 1 also comprises a compartment 6 interposed between the lower layer 2 and the upper layer 3. In particular, the compartment 6 faces the surface 2*b* and the surface 3*a* of the lower 2 and upper 3 layers.

Preferably, the compartment 6 seamlessly extends between the lower layer 2 and the upper layer 3 throughout the extension of the lower layer 2 and the upper layer 3.

The compartment 6 comprises a filler medium 7 configured to emit an optical emission beam E when lit by an incident optical beam I. For example, the filler medium 7 is a fluorescent polymer.

In accordance with a preferred embodiment, the filler medium 7 is a substance in solid form. In accordance with another alternative embodiment, the filler medium 7 is a substance in liquid or gel form.

The compartment 6 also comprises markers M, homogeneously dispersed in the filler medium 7. The markers M have a predefined molecular weight and dimensions. Preferably, the markers M are ions of a salt dissolved in the filler medium 7.

It should be noted that the markers M have a predefined electrical charge and are adapted to move in the presence of an electrical signal. In particular, when an electrical signal is applied to the first portions 4, the markers M move inside the compartment 6 in variable amounts in all directions according to the intensity of the electrical signal applied. Depending on the sign and on the electric charge module, the movement of the markers M inside the compartment 6 varies, and consequently the local concentration of markers M inside the compartment 6 varies. The filler medium 7 is configured to interact with the markers M. Depending on the local concentration of the markers M, the filler medium 7 is configured to increase or decrease the intensity of the optical emission beam E.

According to a preferred embodiment of the invention, the upper layer 3 comprises an upper electrode 8. Preferably, the first portions 4 comprise a plurality of upper electrodes 8. More preferably, the first portions 4 consist of a plurality of upper electrodes 8. Each upper electrode 8 is configured to receive a respective electrical signal.

Preferably, the upper electrodes 8 may have different shapes, as shown in FIGS. 1*a* and 1*b*. For example, the upper electrodes 8 have a conformation selected from plate, polygonal, spheroidal or a combination thereof.

The lower layer 2 comprises a lower electrode 9. In particular, the lower layer 2 consists of a single lower electrode 9.

The upper electrodes 8 and the lower electrode 9 are electrically connected between them in an electric circuit or are floating.

According to a preferred embodiment shown in FIG. 3, the first portions 4 are configured to house at least a cell C. In particular, the cells C are arranged above the first portions 4. Preferably, the first portions 4 have such dimensions as to house one single cell C each. More preferably, the first portions 4 comprise a plurality of micro-electrodes or nano-electrodes each adapted to house a cell C or a portion of cell C. In accordance with this preferred embodiment, the first portions 4 are configured to receive the electrical signal of the action potential generated by the excited cell C.

Upon application of the electrical signal to the first portions 4, the markers M inside the compartment 6 are attracted or rejected by a first portion 4 on the basis of the sign of the potential applied thereto and on the basis of the electrical charge of the markers M. Accordingly, the markers M move along the field lines toward the first portions 4 by which they are attracted. In particular, the markers M move from and towards zones Z defined inside the compartment 6 and underlying the respective first portions 4 by which the markers M are rejected or attracted. Consequently, the concentration of the markers M in the various zones Z indicates the real-time electrical charge present in the first portions 4 by which the markers M are rejected or attracted.

The filler medium 7, when it is hit by the incident optical beam I by an optical source 10, emits an optical emission beam E. The filler means 7, moreover, interacts with the markers M present in the compartment 6. Preferably, the filler medium 7 increases or decreases the intensity of the optical emission beam E, emitted by the filler medium 7, depending on the local concentration of the markers M in the compartment 6. In other words, the filler medium 7 has a stronger interaction with the markers M where they are more concentrated. Therefore, the effect of increasing or decreasing the intensity of the optical emission beam E is more visible at the points where the markers M are accumulated with a higher density. Furthermore, by suitably selecting the filler medium 7 and the markers M, it is possible to determine how the intensity of the optical emission beam E is increased or decreased by the interaction of the filler medium 7 with the markers M.

The optical emission beam E crosses the lower layer 2 starting from the surface 2b and can be received by an external detection optical device 11.

It should be noted that the optical source 10 is preferably external to the microfluidic device 1. According to an alternative embodiment, the optical source 10 is internal to the microfluidic device 1, i.e. integrated therewith, and comprises, for example, micro-LED or other similar technologies known per se.

The intensity of the optical emission beam E depends on the concentration of the markers M in a given zone Z. Therefore, from the light signal detected by the detection optical device 11 it is possible to observe the behaviour of the electrical signal applied on the first portions 4. In the case where the electrical signal is generated by a single cell C, it is possible to observe the trend of the action potential of said cell C.

The microfluidic device 1, with respect to the devices known in the state of the art or to the one described in the above-mentioned patent application, allows to obtain a good spatial resolution, thanks to the homogeneous structure that it has, and in particular to the compartment 6 which seamlessly extends between the lower layer 2 and the upper layer 3.

According to a preferred embodiment, the first portions 4 are at least partially reflective with respect to the incident optical beam I. Preferably, at least the surfaces of the first portions 4 facing the compartment 6 are reflective with respect to the incident optical beam I. Advantageously, it is possible to intensify the emission effect of the filler medium 7, since it is also lit by the reflected incident optical beam I.

According to a preferred embodiment, the second portions 5 are transparent with respect to the optical emission beam E. According to this embodiment, the optical emission beam E emitted by the filler medium 7 can also be detected through the upper layer 3 at the second portions 5. Advantageously, it is possible to observe the movements of the markers M also below the second portions 5 in order to obtain a complete vision over time of the movement of the markers M inside the compartment 6 according to the applied electrical signal. As a result, it is possible to have precise information on the mode and rate of propagation of the action potential of a cell C.

According to an embodiment that is alternative to the preceding one, the second portions 5 are at least partially reflective with respect to the incident optical beam I. This advantageously allows to intensify the emission effect of the filler medium 7, since it is also lit by the reflected incident optical beam I. According to this embodiment, the optical emission beam E is detected on the side of the lower layer 2, as occurs for the detection below the first portions 4. Advantageously, it is possible to observe the movements of the markers M also below the second portions 5 in order to obtain a complete vision over time of the movement of the markers M inside the compartment 6 according to the applied electrical signal. As a result, it is possible to have precise information on the mode and rate of propagation of the action potential of a cell C.

With particular reference to FIG. 4a, it should be noted a typical action potential signal, which is then converted into the optical signal shown in FIG. 4b.

As described above, the markers M have the possibility of moving inside the compartment 6 according to the electric potential applied to the first portions 4 and to the electrical charge, molecular weight and concentration of the markers M.

If the filler medium 7 is a liquid, in the presence of an electrical signal applied to the first portions 4 in the form of a pulse, the markers M move in the compartment 6 during the rising edge of the electrical signal and during the falling edge of the applied electrical signal. In this configuration, the optical emission beam E generated by the filler medium 7 and amplified/reduced by the markers M in the zones Z allows to generate an optical signal representative of the pulse shape of the electrical signal applied to the first portions 4.

If the filler medium 7 is a gel or a solid, the markers M have the possibility of moving inside the compartment 6 in the presence of an applied electrical signal but they maintain their position in the compartment 6 in the absence of an electrical signal. The markers M maintain in any case the possibility of moving among the various zones Z in the presence of an electrical signal of sufficient intensity and opposite sign.

This solution is particularly advantageous for the realisation of optical read non-volatile memories with very low activation voltages of the order of a few mV. In fact, the markers M remain in a fixed position in the zones Z of the compartment 6. The detected optical emission beam E therefore remains constant by virtue of the position of the markers M and can be read several times, through the detection optical device 11.

It should be noted that the microfluidic device 1 of the present invention can also be used for realising a neuromorphic chip. In this configuration, each zone Z underlying an upper electrode 8 can represent a memory unit, for example a bit, whose value can be modified, i.e. written with a few mV applied to the first portions 4 and read, in optical mode, through the detection optical device 11. In greater detail, according to this configuration, the detected light signal, i.e. the intensity of the optical emission beam E coming from each zone Z, can assume intensity values that are not discrete but continuous within a predetermined range. This range varies according to the concentration of the markers M in the zone Z, in particular it varies between 0, in which no markers M are present inside the zone Z, and a value given by the maximum concentration of markers M inside the zone Z.

In particular, the application of data storage by means of the microfluidic device 1 as described above is carried out by means of an electrical writing step of a data item and an optical reading step of the written data item.

In detail, the electrical writing of the data item is obtained by applying to the upper layer 3 an electrical signal, according to the intensity and in which direction the markers M move in variable amounts inside the filler medium 7. At the end of the application of the electrical signal, due to the gel or solid nature of the filler medium 7, the markers M remain stationary in the position in which they are located. Accordingly, the amounts of markers M that accumulate in the different zones Z of the compartment 6 indicate the applied potential and represent the stored data item.

It should be noted that, for this application, the electric potential pulses for writing the data item are generated by potential sources which are external to the microfluidic device 1, or alternatively by cells placed on the first portions 4, like for the application described above concerning the measurement of the cellular action potential.

The optical reading of the data item is carried out by illuminating the lower layer 2 with an incident optical beam I and by detecting the optical emission beam E emitted by the markers M accumulated in the different zones Z of the compartment 6. The intensity of the optical emission beam E coming from the various zones Z is proportional to the amount of markers M present, and therefore allows to read the stored data.

By way of example, if the electrical signal empties a zone Z from the markers M, the resulting optical emission beam E, relative to that zone Z, will be low and may be associated with the logic bit 0. If the electrical signal fills a respective zone Z with markers M, the resulting optical emission beam E, relative to that zone Z, will be high and can be associated with the logic bit 1. In the example in question, it should be noted how the sequential writing/reading of the zones Z, to which a respective logic number 0/1 is assigned, allows the data to be stored according to the binary code.

According to a particular embodiment, the microfluidic device 1 comprises markers M having molecular weight and/or dimensions and/or electrical charge and/or hydrodynamic radius different from each other.

In particular, the hydrodynamic radius is indicative of the friction due to the fluid to which the markers M are subjected, i.e., the speed at which the markers M move.

Markers M having different values of molecular weight and/or dimensions and/or shape and/or electrical charge and/or hydrodynamic radius will consequently move differently inside the compartment 6. Therefore, it is possible to obtain continuous values and hence more precise measurements. In the case of measuring the action potential, for example, it is possible to measure both fast and low intensity potentials as well as longer and intense action potentials. Advantageously, it is possible to realise a memory with multi-state bits. It should be pointed out that in the case of application for memories, the potential can also be external and therefore not necessarily generated by a biological element, such as the cell C.

It is also an object of the present invention an apparatus, indicated with 100 in FIGS. 2-3, comprising the microfluidic device 1 according to the second embodiment, an optical source 10 and a detection optical device 11.

The optical source 10 is configured to emit an incident optical beam I towards the lower layer 2, and preferably towards the lower surface 2a. Specifically, the optical source 10 is configured to direct the incident optical beam I towards the lower surface 2 at least at the first portions 4 of the microfluidic device 1, that is, at the zones Z that attract or reject the markers M.

The detection optical device 11, configured to detect the optical emission beam E, emitted by the filler medium 7, is a CCD or CMOS device or a detector matrix. Preferably, the detection optical device 11 is filtered along the emission wavelength of the filler medium 7 so as to generate an optical signal representative of the electrical signal applied to the first portions 4, and optionally to the second portions 5, according to the intensity of the detected optical signal, that is, the optical emission beam E.

The present invention also relates to a method for storing data using the microfluidic device 1. In particular, this method is applicable for both embodiments of the microfluidic device 1 described above. As stated above, for the application of this method, the filler medium 7 of the microfluidic device 1 is made in solid or gel form.

This method comprises the step of generating a plurality of electrical signals on the first portions 4.

Moreover, the method comprises the step of generating the incident optical beam I by means of an optical source 10.

The method also comprises the step of receiving the optical emission beam E and filtering a predetermined wavelength of the optical emission beam E by means of a detection optical device 11.

The method for storing data further comprises a step of associating to each zone Z a logic number according to the intensity of the optical emission beam E coming from the zones Z. In other words, according to the concentration of the markers M in a respective zone Z, a logical number is associated with each zone Z.

In particular, the set in sequence of the logical numbers associated with the zones Z, present in the compartment 6 in relation to the first portions 4, gives rise to one or more codes representing the stored data item. In order to read the stored data item, the logical numbers assigned to each zone Z are read in sequence according to the arrangement of the zones Z in the microfluidic device 1.

According to an embodiment, this first step comprises a sub-step of associating the logic number 0 when the concentration of the markers M in the zone Z is zero. In particular, it is assumed that the concentration of the markers M is zero when no markers M are present in the zone Z or when the number of markers M present in the zone Z is lower than a predetermined value. This first step further comprises a sub-step of associating the logic number 1 when the concentration of the markers M in the zone Z is maximum. In particular, it is assumed that the concentration of the markers M is maximum when all the markers M are distributed inside the zones Z, or when the number of markers M present in a respective zone Z is greater than a predetermined value.

In accordance with this embodiment, the code representing the stored data item, obtained by means of the sequential reading of the logical numbers assigned to the zones Z, is a binary code.

The present invention also relates to a method for measuring the action potential of a cell C using the apparatus 100. In particular, this method can be applied to both the embodiments of the microfluidic device 1 and the apparatus 100 described above.

This method comprises the step of providing a cell C on a first portion 4.

The method also comprises the step of generating the incident optical beam I by means of the optical source 10.

The method includes the step of receiving the optical emission beam E and filtering a predetermined wavelength of the optical emission beam E by means of the detection optical device 11.

Advantageously, the method allows to detect the action potential of a cell C in a precise and complete manner, with no need to make structural modifications to the cell C and with no need to use electrical circuits.

A method for realising the microfluidic device 1 of the present invention is described below. In particular, this embodiment is applicable for both embodiments of the microfluidic device 1 described above.

The microfluidic device 1 has a structural configuration such that it comprises two initially separate parts, which are assembled into a multilayer during the manufacturing process described below.

The first part comprises the lower layer 2. In particular, a substrate 12 preferably of glass is coated with a transparent conductive layer on its upper part, i.e. the lower layer 2. The latter is preferably made of indium tin oxide, i.e., indium oxide doped with tin ITO.

The second part comprises the upper layer 3. In particular, the alternation of the first conductive portions 4 with the second insulating portions 5 is made. The first portions 4 are upper electrodes 8, preferably of gold.

Subsequently, a drop of fluid filler medium 7 containing fluorophores and/or other markers M is deposited on the lower layer 2, i.e. on the ITO-coated glass substrate 12. For the final assembly of the microfluidic device 1, the second part comprising the upper layer 3 is positioned and joined to the first part consisting of the lower layer 2, so as to combine the two parts of the multilayer together to form the microfluidic device 1 shown in FIGS. 2-3. In this way, the fluid with fluorophores is trapped between the two lower 2 and upper 3 layers.

The invention claimed is:

1. A microfluidic device comprising:
a lower layer that is electrically conductive and transparent with respect to an incident optical beam,
an upper layer, comprising
first portions that are electrically conductive and configured to receive an electrical signal, and
second portions that are electrically insulating, the first and second portions being adjacent and alternated between them,
a compartment interposed between the lower layer and the upper layer throughout the extension of the lower layer and of the upper layer and seamlessly extending between the lower layer and the upper layer, the compartment containing a filler medium configured to emit an optical emission beam when lit by an incident optical beam and markers dispersed in the filler medium,
wherein
the markers are electrically charged and are adapted to move inside the compartment in all directions in variable amounts according to the intensity of the electrical signal applied to one or more of the first portions, the filler medium being configured to interact with the markers to increase or reduce the intensity of the optical emission beam depending on the local concentration of markers in the compartment, and

the first portions are spaced between them at a distance between 1 and 100 μm.

2. The microfluidic device according to claim 1, wherein the first portions are at least partially reflective with respect to the incident optical beam.

3. The microfluidic device according to claim 1, wherein the second portions are transparent with respect to the optical emission beam.

4. The microfluidic device according to claim 1, wherein the second portions are at least partially reflective with respect to the incident optical beam.

5. The microfluidic device according to claim 1, wherein
the first portions comprise a plurality of upper electrodes, each upper electrode being configured to receive a respective electrical signal,
the lower layer consists of a single lower electrode.

6. The microfluidic device according to claim 5, wherein upper electrodes have a conformation selected from plate, polygonal, spheroidal or a combination thereof.

7. The microfluidic device according to claim 5, wherein the upper electrodes and the lower electrode are electrically connected between them in an electric circuit or are floating.

8. The microfluidic device according to claim 1, wherein the markers are ions of salts of predefined dimensions and/or molecular weight and/or electrical charge and/or hydrodynamic radius.

9. The microfluidic device according to claim 1, wherein the filler medium is a substance in solid form.

10. The microfluidic device according to claim 1, wherein each first portion is configured to house at least a cell and to receive an electrical signal of the action potential generated by the excited cell.

11. The microfluidic device according to claim 1, wherein the first portions have such dimensions as to house one single cell each.

12. An apparatus comprising:
a microfluidic device according to claim 1,
an optical source configured to emit an incident optical beam towards the lower layer at least at the first portions of the microfluidic device,
a detection optical device configured to receive an optical emission beam generated by the filler medium.

13. A method for measuring the action potential of a cell using an apparatus according to claim 12, comprising the steps of:
providing a cell on a first portion,
generating the incident optical beam by means of an optical source,
receiving the optical emission beam and filtering a predefined wavelength of the optical emission beam.

14. A method for storing data by the apparatus according to claim 12, wherein the markers move to and from zones defined inside the compartment and underlying the respective first portions, said method comprising the steps of:
generating a plurality of electrical signals on the first portions,
generating the incident optical beam by means of an optical source,
receiving the optical emission beam and filtering a predefined wavelength of the optical emission beam,
associating to each zone a logical number according to the intensity of the optical emission beam coming from the zones.

* * * * *